US008187184B2

(12) United States Patent
Muller et al.

(10) Patent No.: US 8,187,184 B2
(45) Date of Patent: May 29, 2012

(54) ACCESS DISCONNECT SYSTEM WITH OPTICAL AND OTHER SENSORS

(75) Inventors: Matthew R. Muller, Lindenhurst, IL (US); Luke Beehner, Milwaukee, WI (US); William W. Chan, Lake in the Hills, IL (US); James S. Slepicka, Genoa City, WI (US); Atif Yardimci, Vernon Hills, IL (US)

(73) Assignees: Baxter International, Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 1285 days.

(21) Appl. No.: 11/859,556

(22) Filed: Sep. 21, 2007

(65) Prior Publication Data

US 2009/0082649 A1    Mar. 26, 2009

(51) Int. Cl.
*A61B 5/00* (2006.01)
(52) U.S. Cl. ....................................................... 600/371
(58) Field of Classification Search ................... 600/371; 128/899; 604/4.01–6.16
See application file for complete search history.

(56) References Cited

U.S. PATENT DOCUMENTS

| 4,181,610 | A | | 1/1980 | Shintani et al. |
| 4,773,422 | A | * | 9/1988 | Isaacson et al. ............. 600/326 |
| 4,927,264 | A | * | 5/1990 | Shiga et al. ..................... 356/41 |
| 5,200,627 | A | | 4/1993 | Chevallet |
| 5,670,050 | A | | 9/1997 | Brose et al. |
| 5,910,252 | A | | 6/1999 | Truitt et al. |
| 6,009,339 | A | | 12/1999 | Bentsen et al. |
| 6,073,043 | A | * | 6/2000 | Schneider ..................... 600/424 |
| 6,208,880 | B1 | | 3/2001 | Bentsen et al. |
| 6,246,482 | B1 | | 6/2001 | Kinrot et al. |
| 6,445,304 | B1 | | 9/2002 | Bandeian, Jr. et al. |
| 6,461,329 | B1 | | 10/2002 | Van Antwerp et al. |
| 6,683,679 | B2 | | 1/2004 | Belenkii |
| 6,752,785 | B2 | | 6/2004 | Van Antwerp et al. |
| 6,806,947 | B1 | | 10/2004 | Ekdahl et al. |

(Continued)

FOREIGN PATENT DOCUMENTS

DE    4432348 A1    2/1995

(Continued)

OTHER PUBLICATIONS

Roggan, Andre et al., "Optical Properties of Circulating Human Blood in the Wavelength Range 400-2500 NM", Jan. 1999, Journal of Biomedical Optics, vol. 4 No. 1, pp. 36-46.*

(Continued)

*Primary Examiner* — Patricia Mallari
*Assistant Examiner* — Christian Jang
(74) *Attorney, Agent, or Firm* — K&L Gates LLP

(57) ABSTRACT

An optical access disconnect system is useful for detecting the presence of blood. The optical access disconnect system includes one or more optical sensors placed near an access site of a patient, the optical sensors suitable for detecting the presence of blood, especially by detecting a difference in light reflected or absorbed by blood. The optical access disconnect system may also be used as an interlock to assure compliance. A detector may be placed adjacent the access site to detect the access needle, or an object or mark on the access needle or fluid line. A therapy machine, such as a dialysis machine, may be programmed not to start or continue operation unless the needle or fluid line is detected. The detector may be one of the optical sensors, calibrated or adjusted to detect a mark on the needle or access line, or may be another type of detector.

20 Claims, 12 Drawing Sheets

U.S. PATENT DOCUMENTS

| | | |
|---|---|---|
| 6,947,131 B2 | 9/2005 | O'Mahony et al. |
| 6,979,306 B2 | 12/2005 | Moll |
| 7,230,687 B2 | 6/2007 | O'Mahony et al. |
| 7,276,041 B2 | 10/2007 | Moll |
| 7,605,710 B2 * | 10/2009 | Crnkovich et al. ........... 340/604 |
| 7,947,033 B2 * | 5/2011 | Ganapathy et al. ........... 604/543 |
| 2002/0198483 A1 * | 12/2002 | Wariar et al. ................. 604/5.01 |
| 2003/0195453 A1 * | 10/2003 | Han et al. ..................... 604/5.01 |
| 2004/0079687 A1 | 4/2004 | Muller et al. |
| 2005/0038325 A1 * | 2/2005 | Moll ............................. 600/300 |
| 2006/0130591 A1 | 6/2006 | Perkins |
| 2007/0004996 A1 | 1/2007 | Lovejoy et al. |
| 2008/0065006 A1 | 3/2008 | Roger |
| 2008/0195021 A1 | 8/2008 | Roger |
| 2008/0195060 A1 * | 8/2008 | Roger et al. .................. 604/246 |
| 2009/0079578 A1 | 3/2009 | Dvorsky |
| 2009/0080757 A1 | 3/2009 | Roger |
| 2009/0082646 A1 | 3/2009 | Bouton |
| 2009/0082647 A1 | 3/2009 | Busby |
| 2009/0082653 A1 | 3/2009 | Rohde |
| 2009/0082676 A1 | 3/2009 | Bennison |
| 2009/0088612 A1 | 4/2009 | Bouton |
| 2009/0088613 A1 | 4/2009 | Marttila |
| 2009/0088683 A1 | 4/2009 | Roger |
| 2009/0105627 A1 | 4/2009 | Rohde |
| 2009/0145446 A1 * | 6/2009 | DeDecker ..................... 128/899 |
| 2010/0022934 A1 | 1/2010 | Hogard |
| 2010/0022935 A1 | 1/2010 | Muller |
| 2010/0087770 A1 * | 4/2010 | Bock et al. ................... 604/4.01 |

FOREIGN PATENT DOCUMENTS

| | | | |
|---|---|---|---|
| DE | 19802985 | A1 | 7/1999 |
| EP | 1736185 | A2 * | 12/2006 |
| EP | 1892001 | A1 | 2/2008 |
| WO | 99/24145 | A1 | 5/1999 |
| WO | 2006/001759 | | 1/2006 |
| WO | WO 2006001759 | A1 * | 1/2006 |
| WO | 2007/059472 | A2 | 5/2007 |
| WO | 2008/021462 | A2 | 2/2008 |

OTHER PUBLICATIONS

PCT/US2008/066042, Sep. 19, 2008 (mailing date), Baxter International, Inc.

* cited by examiner

ACCESS DISCONNECT SYSTEM WITH OPTICAL AND OTHER SENSORS

BACKGROUND

The invention is in the field of medical treatments generally and patient vascular access systems. The present invention relates to embodiments of a method and a system for detecting disconnection of an access needle or catheter during treatment.

The maxim of "first, do no harm," may be a good summary of the Hippocratic oath required of doctors and practiced by medical professionals. Nowhere is this principle required more than in modern medicine. With patients living longer, there are more extended treatments and more frail patients than ever. Such patients are in danger from a number of complications that can arise from continuing therapeutic procedures, and even from diagnostic procedures, that are necessary for their continued care. Treatments involving extracorporeal blood treatment are clear examples.

The most obvious danger is infection, but the harm caused by infection can be overcome by not re-using even supposedly-sterile devices and by diligent attention by the patient himself or herself, and by care givers attending to the patient. Other dangers also arise, but, like infections, have been difficult to eradicate. One of these dangers arises in blood treatment procedures in which the blood of a patient is physically removed from the patient for treatment, and then returned, all in the same procedure. Removal and return of blood is practiced in hemodialysis, for those persons whose kidneys do not function well. Other procedures, such as apheresis, involve removing blood from a patient or a donor to separate blood platelets or plasma from the red blood cells and then returning the red blood cells to the patient or donor, as described in U.S. Pat. Nos. 5,427,695 and 6,071,421.

The extracorporeal medical treatments described above require that the blood be removed for treatment and then returned. This requires access to the patient's vascular system, from which blood is removed and to which blood is then returned. If a "batch" treatment is used, that is, a quantity of blood is withdrawn, treated and returned, only a single needle is used. Each batch of such treatment is typically short, and the treatment is attended by a medical professional at a clinic or hospital. A variation on the batch treatment is a "batch" continuous method in which only a single needle is used. There are distinct withdraw and return phases in a batch continuous process. During the draw phase, blood is processed and additional blood is sent to a holding container to be processed during the return phase. In the return phase, blood is processed from the holding container and then returned to the patient or donor through the single needle.

Other treatments are continuous, such as the platelet separation discussed above, or dialysis treatment, and may require a duration of several hours or even overnight.

Continuous treatments require two needles, or access points, one for withdrawal of blood and one for return. The withdrawal site is normally an artery, and a needle and a pump are used to provide the blood to the therapeutic machine. It is relatively simple to detect a problem withdrawal, for instance, if the withdrawal needle is dislodged, using conventional air sensor technology. Detecting a problem in the return of the blood to the patient is more difficult. The return line typically includes a needle with venous access. If the return line is dislodged, the blood is not returned to the patient, but may continue to be pumped and may accumulate near the patient, but not returned to the patient's vascular system. Depending on the pumping rate of the blood and the time for treatment, this could have life-threatening effects on the patient within a very short period of time.

Accordingly, a number of apparatuses have been devised for detecting needle dislodgement, especially venous dislodgement. An example is U.S. Pat. Appl. Publ. 2006/0130591. In a device according to this application, a venous needle is equipped with a photosensor and is covered with an opaque patch. This device would not send a signal or an alarm if the needle begins leaking or is only slightly dislodged. In this example, the photosensor could still fail to detect light because the needle has not been dislodged sufficiently to expose the photosensor to light. In addition, this method requires ambient light and would thus not be suitable for patients that cover their arm with a blanket or who perform nocturnal dialysis while sleeping in a dark bedroom.

Numerous other techniques have been devised, many of them depending on a flow of blood causing conductivity between two electrodes or two wires. What is needed is a better way of quickly detecting dislodgement of a venous or other needle from a patient, so that inadvertent loss of blood and harm to the patient is avoided.

SUMMARY

A first embodiment is an optical access disconnect system. The optical access disconnect system includes at least one first optical detector, a mount suitable for mounting the at least one first optical detector, signal processing circuitry, the circuitry operably connected to the at least one first optical detector, and a communications circuit connected to the signal processing circuitry, wherein the mount and the at least one first optical detector are configured for positioning adjacent a dialysis access site for detecting a presence of blood of a patient.

A second embodiment is an optical access disconnect system. The optical access disconnect system includes at least one optical sensor, a mount suitable for mounting the at least one optical sensor on a patient, wherein the mount and the at least one sensor are configured for positioning adjacent an access site for detecting a presence of blood. The system also includes signal processing circuitry operably connected to the at least one optical sensor, a communications circuit connected to the signal processing circuitry, and an output device connected to the communications circuit or to the signal processing circuitry, the output device configured for sending a signal if blood is detected.

Another embodiment is an optical access disconnect system. The optical access disconnect system includes at least one optical sensor, a mount suitable for mounting the at least one optical sensor, wherein the mount and the at least one optical sensor are configured for positioning adjacent a dialysis access site on a patient for detecting a presence of blood, signal processing circuitry operably connected to the at least one optical sensor, a detector for detecting a presence of a needle adjacent the access site, the detector operably connected to the processing circuitry or a control circuit in communication with the signal processing circuitry, and a communications circuit connected to the signal processing circuitry.

Another embodiment is a method for detecting a presence of blood. The method includes steps of furnishing an optical access disconnect detecting system, the system comprising one or more optical sensors, mounting the one or more optical sensors near an access site of a patient, initiating a medical therapeutic procedure at the access site, operating the one or more optical sensors to detect a presence of blood, and sending a signal if the presence of blood is detected.

Another embodiment is an access disconnect system. The access disconnect system comprises a detector on a mount suitable for mounting on a patient, wherein the mount and the detector are configured for positioning adjacent an access site for detecting an access needle or tubing connected to the access needle, wherein the detector is selected from the group consisting of an optical detector, a proximity detector and a hall-effect sensor, wherein the access needle or the tubing comprises a detectable feature, the feature selected from the group consisting of a mark, a metal piece, and a magnet. The access disconnect system also comprises signal processing circuitry operably connected to the detector, and an output device connected to the signal processing circuitry, the output device configured for sending a signal if the detector ceases to detect the feature.

Another embodiment is a method for detecting an access needle. The method includes steps of furnishing a detector mounted on a patient near an access site, the detector suitable for detecting a feature on an access needle or on tubing for the access needle, the feature selected from the group consisting of a mark, a metal object, and a magnet, and attaching the access needle and the tubing to the access site. The method also includes steps of detecting the feature with the detector, initiating a therapeutic procedure at the access site, monitoring a presence of the feature with the detector, and sending a signal if the feature ceases to be detected.

Additional features and advantages are described herein, and will be apparent from, the following Detailed Description and the figures.

DETAILED DESCRIPTION

There are numerous embodiments of the present invention, only a few of which are described herein. The present patent focuses on the use of embodiments of the invention for dialysis needle access in a patient. However, the invention may be used in many other ways. For instance, blood leakage may be detected in other sites of patients and for other purposes, such as blood plasma processing, blood donation, transfusions, or any other procedure in which blood is removed from a person in significant, often life-determining, quantities.

As noted above, persons undergoing hemodialysis could lose very large quantities of blood if for any reason the return needle becomes dislodged. Blood has optical properties, such as absorbance and reflectance, that are very different from what should be the normal properties of the surrounding tissue or access site. For example, flesh of all people has a color that is distinct and different from that of blood, which normally has a red color. A fistula dialysis access site, or other access site, such as one for blood processing, will frequently be covered or protected with white gauze. If blood leaks from the site, the gauze will absorb the blood and its color will change. Thus, an optical detector, especially one that is "tuned" for detection of blood, will be able to detect the change in color.

An optical detector may be optimized for detecting blood by taking advantage of the ability of blood to absorb light of lower wavelengths, such as light with wavelengths between about 405 nm and about 532 nm. Thus, if there is a decrease of light at these wavelengths that is detected by an optical sensor, this may be an indication of the presence of blood. On the contrary side, blood tends to reflect light at higher wavelengths, such as light having a wavelength of greater than 600 nm, such as about 800 nm. Thus, an increase in detection of light of over 600 nm, such as 800 nm, may indicate a presence of blood.

Figure 1:
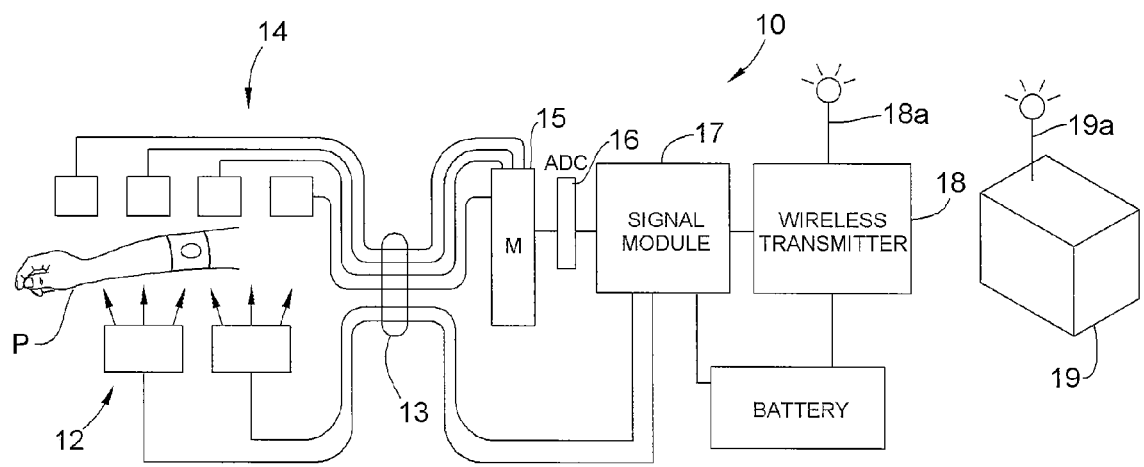
FIG. 1 is a first embodiment of an optical disconnect system.
Figure 4:
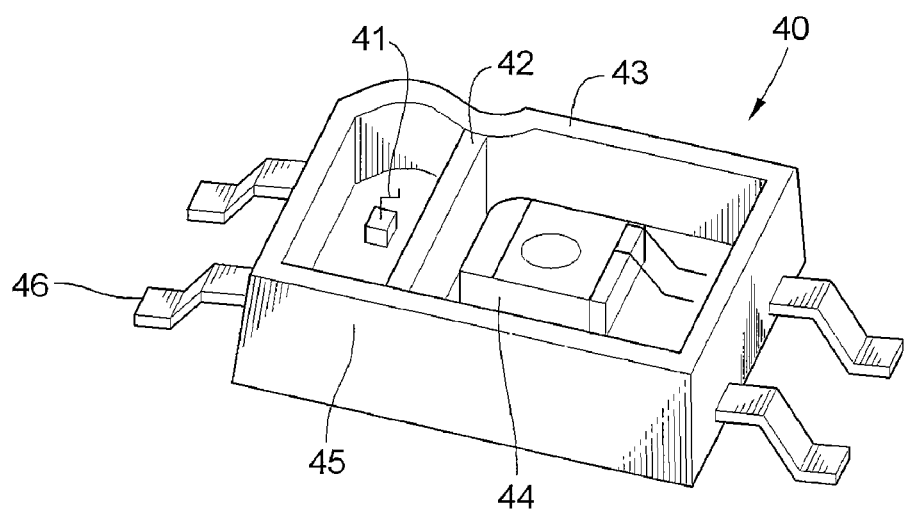
FIG. 4 is an optical sensor.

A first embodiment of a system for detecting leaks or disconnects with an optical detector is depicted in FIG. 1. Access disconnect system 10 includes signal processing within a housing. The signal module, part of the signal processing circuitry, connects to one or more light emitters 12. The light emitters may each have a separate wavelength or range, such as about 405 nm, about 532 nm, about 580 nm, or about 645 nm. The light emitters could instead all emit light of about the same range, for instance at about 425 nm. This wavelength occurs at the isosbestic point of blood, that is, the point at which oxygenated and non-oxygenated blood absorb light about equally. This is a very good wavelength for detecting blood, because light at 425 nm will be selectively absorbed, and detectors will note a decrease in the amount of available light of this wavelength. This wavelength is also important because it has a local maximum for the spectral absorbance of hemoglobin, that is, this is a wavelength at which an optical sensor would be maximally sensitive to the presence of hemoglobin. Signals to and from the light sensors are carried by wires in cable 13, which connects sensors or detectors 14 to signal processing electronics 15, 16, 17. The emitted light is detected by light sensors or detectors 14. The light emitters and detectors may both be part of the same light sensor, as depicted in FIG. 4. System 10 also includes a battery power supply, the battery located with the signal electronics.

Signals from the light sensors or detectors 14 are processed by a multiplexer 15 and may be converted from analog to digital signals by an ADC converter 16. The signals are then processed by signal module 17. Signal module 17 may include further signal processing, such as by a DSP, or it may simply take the converted signal data and transmit the data via a transmitter 18 and antenna 18a to a remote processor 19 through its antenna 19a. FIG. 1 depicts wireless transmission, but the signal module could instead be connected to a remote site via an electrical wire or optical fiber. In this embodiment, signal module 17 does not further process the converted signals, but converts the signals for transmission. All further data processing, and conversion of the digitized data to useful information, such as whether or not the signals suggest a blood leak, is accomplished at the remote location.

The signal processing circuitry and wireless transmitter are small and compact, and are easily placed on the patient at the access site. One module that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). One or more optical sensors are connected to the module. The module in FIG. 1 includes a multiplexer and an ADC converter to convert analog data from the detectors of the sensors into digital data. The digital data is thus formatted, at least by sensor, when it is routed to a data buffer before transmission to a remote site.

The remote site, as noted, is very near, within range of the ZigBee module, about 10-20 feet. Thus, the local portion or signal module is conveniently small and unobtrusive for the patient, while the larger, perhaps bulkier, portion is located remotely but still nearby. The remote portion includes a radio receiver for receiving transmissions from the signal module. The remote portion also includes signal processing circuitry for processing the signal data and a microprocessor or microcontroller for interpreting the processed data.

The microcomputer also includes a computer program and logic for interpreting the processed data and for determining a next step. If the processed data suggests no change and no leak, then the computer takes no action. If the processed data suggests a change, and a leak or the presence of blood, then the data may be recorded in a memory of the remote portion, and a signal may be sent as a result of the detection of a change, a leak, or the presence of blood. The signal may cause an alarm to be sounded to alert the patient or medical personnel to the condition. The signal may instead or in addition send a signal to the hemodialysis machine or blood processing machine to cease pumping blood from the patient. In other applications, the signal may cause other appropriate actions to be taken to alert one or more personnel and to cease whatever medical procedure is taking place to avoid harm to the patient.

Figure 2:
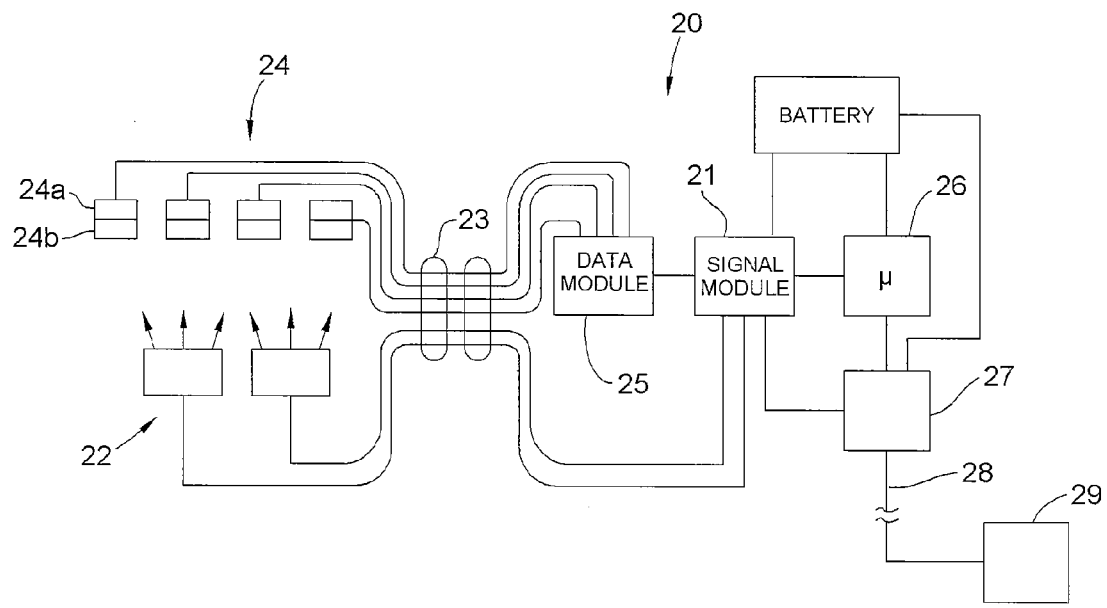
FIG. 2 is a second embodiment of an optical disconnect system.

In other embodiments, the local signal module may include additional circuitry with additional processing capability. For example, the embodiment of FIG. 2 is an access disconnect system 20. Access disconnect system 20 includes a battery, a signal module 21, a data module 25, a microcomputer 27, and additional processing circuitry within the signal module. These components are part of the local module and are connected to the light sensors by a cable 23. The additional processing circuitry, in this embodiment, includes a digital signal processor (DSP) for sensor data processing. Data module 25 also includes a multiplexer and an ADC converter, as described above. The signal module causes periodic light pulses at a rate from about 0.1 Hz to about 1 Hz to be sent from light transmitters 22. The transmitters may be pulsed sequentially or together. Light transmitted is detected by light detectors 24a after the light passes through light filters 24b. The filters are selected to absorb light or block of a wavelength different from the wavelength they emit, and thus to enhance the sensitivity and improve the reliability of the sensors and the access disconnect system. If a filter is not desired, it is also possible to perform the filtering function within the electronics and software by selecting a carrier frequency for the incident illumination and filtering at that frequency in the receiver circuit.

The light that impinges on detectors 24a is converted by the detector to an analog signal that is sent to a light data module 25 within the optical module. Data module 25, with the multiplexer and ADC, converts the analog data to digital data for the microcomputer 27. The microcomputer analyzes the data according to logic that has been programmed into the computer. The microcomputer can then cause a signal to be sent via transmitter 28 to a remote receiver 29 wirelessly or by a wired connection as shown. If a wired connection is used, the embodiment of FIG. 2 can obtain power via the wired connection instead and eliminate the battery component.

The remote receiver 29 is a computer at a hospital or clinic which is performing a procedure for the patient. In other embodiments, the patient may be receiving home care therapy, and the receiver may be located in a home of the patient. The remote receiver then may sound an alarm or cause a dialysis or other machine or pump to cease operation, thus removing the patient from danger. The alarm should be sufficient to alert a home-care patient, or a care-giver, who may be required to take other necessary action to mitigate any adverse health effects. In any event, the therapy in this situation will have ceased, and an alternate or additional course of action may be required to insure that the patient is safe and that the patient still receives the necessary therapy.

Figure 3:
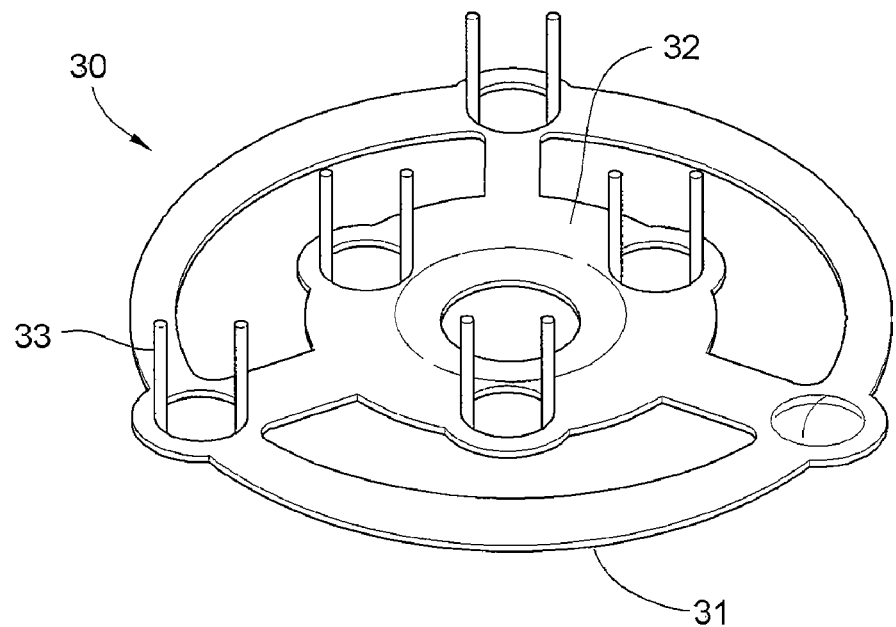
FIG. 3 is an embodiment of a mount for optical sensors or detectors.

In either of the embodiments above, or in alternate embodiments, the light sensors will need to be mounted conveniently for the patient. Only the mount, and the sensors on it, need be mounted directly to the patient. One mount that has been devised is depicted in FIG. 3. Mount 30 includes an outer ring 31, an inner ring 32, and a plurality of individual mounts 33, one for each sensor desired. The outer ring of the mount is about 5 cm in diameter (about 2 inches). The inner ring is about 2.5 cm in diameter (about 1 inch). The mount has been designed so that its very center is located at the access site, with the inner ring 32 of sensors adjacent the access site, and the outer ring 31 of sensors a little further away. The mount is made from soft silicone. Other embodiments may use other materials, such as polyethylene plastic and may be injection molded. Other materials or processes may be used instead. The materials used should be light weight and should conform to the patient's arm or leg.

A typical optical sensor for use with the mount is depicted in FIG. 4. This is a model TRS1755 optical sensor from Texas Advanced Optoelectronics Solutions (TAOS), Plano, Tex., U.S.A. This optical sensor accepts an on signal to emit light. When light quanta are received, the sensor converts the quanta into an analog signal. The light sensor is thus also a light-to-voltage converter, emitting an analog signal. In practice, the light emitting and detecting side of the sensors are mounted facing downward, facing the patient and the access site.

Sensor 40 includes an LED 41, a photodetector 43 and a filter 44 for passing light of the same wavelength it emits. There is also an optical barrier or wall 42 between the diode and the detector, to prevent direct transmission between them. The sensor includes a housing 45 and leads 46 for connecting to sources of power/control, and return signals. The sensor sides are about 4×8 mm, and the sensor is about 1.4 mm thick. Other sensors may be used instead. Other vendors also make photosensors, including photodiodes that emit light and photo detectors for detecting light. An example of a photodiode is the S5821 series from Hamamatsu Corp., Bridgewater, N.J. A photodiode emits a signal in response to observed quanta of light.

Figure 5:
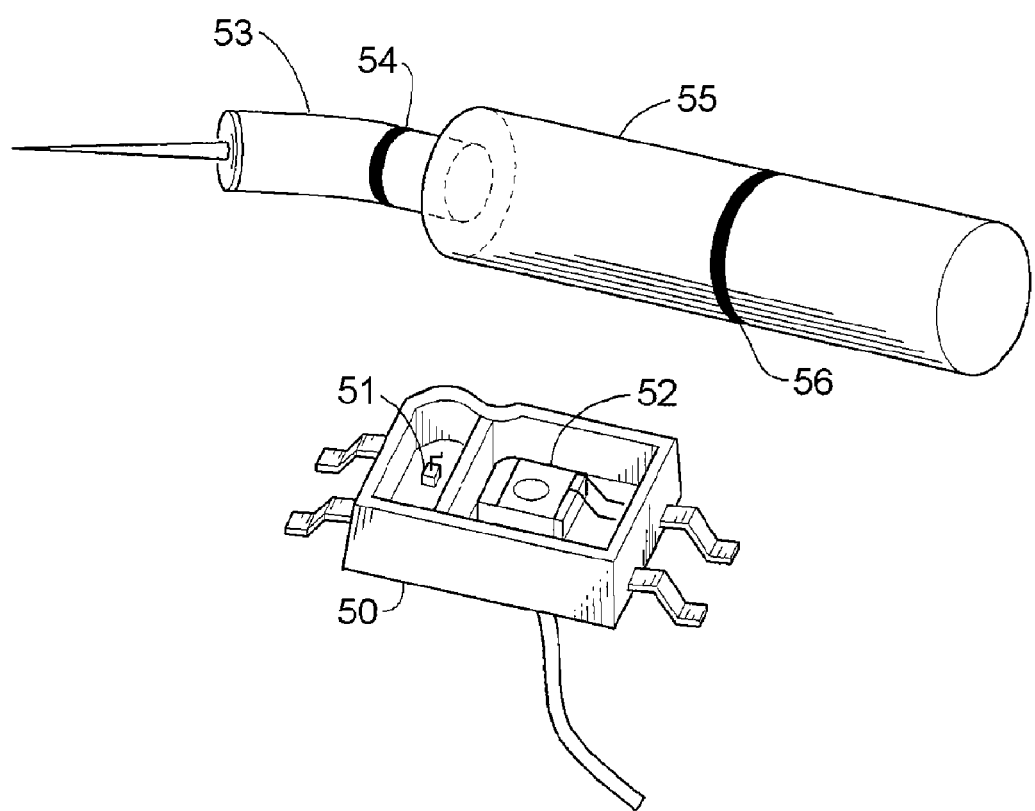
FIG. 5 is a first embodiment of a detector for a needle or an access line.

In addition to the optical detectors discussed above, other types of optical detection may be use to detect the unexpected presence of blood. Another example is depicted in FIG. 5. In this example, a mark 54 is placed on an access needle 53 or a mark 56 is placed on tubing 55 that attaches to the needle. An optical sensor 50, with a light emitter 51 and detector 52 is placed on the patient adjacent the location of the needle or the accessory tubing. The sensor is placed and secured on the patient. The needle and tubing are then advanced, and the placement of the sensor is such that sensor 50 detects a change in the amount of light entering detector 52 as the mark passes the detector. The detector notices the step change in light detected, because the mark is sufficient to cause a noticeable change in the light detected. The placement of the needle and tubing should be made so that the detector sees the mark on needle or tubing, i.e., sees less light when focused on the mark than the detector will see if the needle or tubing shifts more than a slight amount, e.g., more than 2-3 mm.

This detection can be used in two ways. As discussed above, the mark on the needle or other access device, or the mark on the access tubing, may be used to detect dislodgement of the needle or tubing. All other aspects of the embodiments above will remain the same, but the addition of the mark provides an enhancement of the system's ability to detect movement of the needle, rather than the presence of blood.

In addition, the mark and a sensor may be used to ensure compliance of the optical detector. The dialysis machine or other therapeutic device may be programmed so that detection of the mark is required before therapy can begin. Thus, the sensor and the mark act as a gateway or an interlock that must be satisfied before treatment begins. In another embodiment, the system may be programmed so that if the mark is no longer detected, the system reacts as though the needle or the tubing has been dislodged. That is, the sensor and mark function as an optical detector, and if the object being monitored, the mark, moves, the system notes the change in absorption and reacts as though dislodgement has occurred. A signal is sent to the therapy machine to stop pumping blood, and a message is sent to a nurse or appropriate care giver.

Figure 6A:
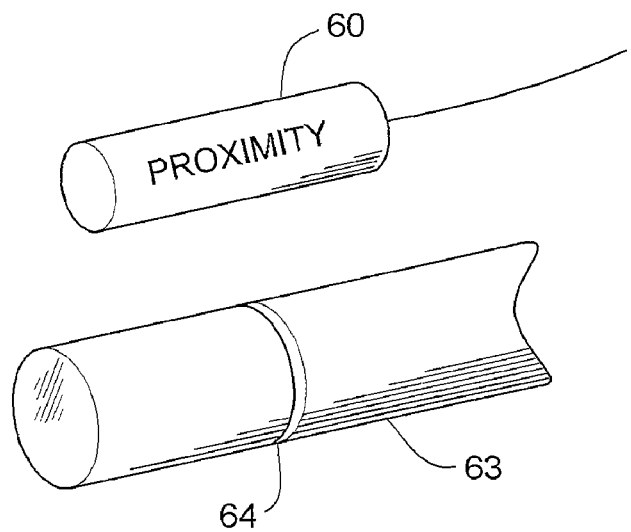
FIGS. 6A, 6B and 7 are additional embodiments of a detector for a needle or access line.
Figure 6B:
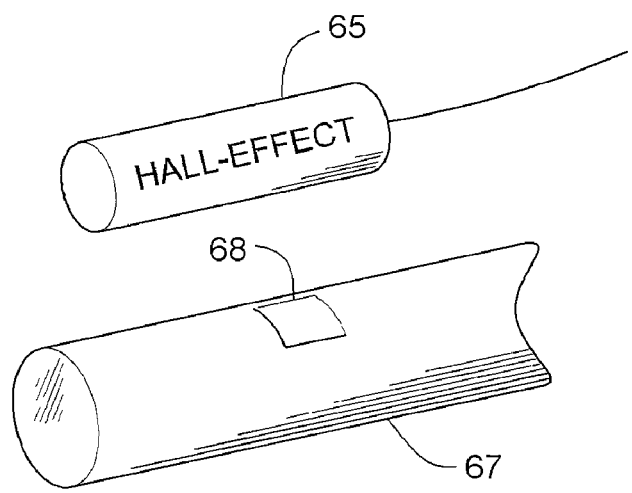
Figure 7:
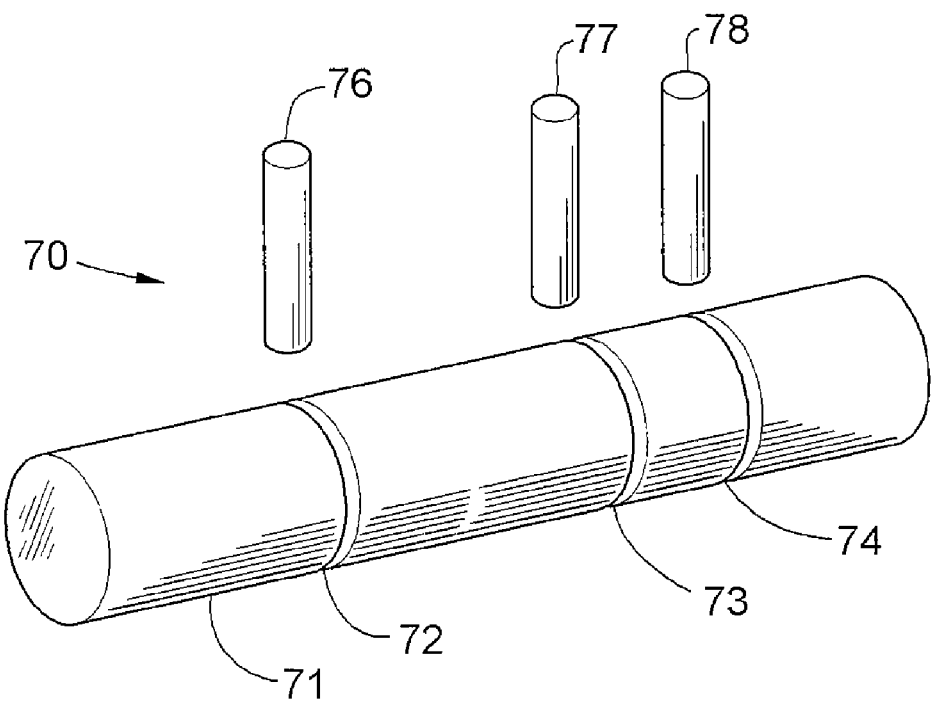

Embodiments of a compliance or interlock system are also possible and are shown in FIGS. 6A, 6B and 7. In FIG. 6A, the mark on the needle or tubing is replaced by a thin band 64 of metal, or other metallic object on the tubing 63. A proximity sensor 60, such as a capacitive sensor or inductive sensor, is mounted on the patient and connected as are the optical sensors. The proximity sensor detects the presence of the metal band as the tubing and access needle are placed into the access site. The dialysis machine or other therapy machine may be interlocked not to begin therapy until the presence of the band has been detected. In another embodiment, the therapy machine may be programmed to periodically check for the presence of the band, and if it is not detected, dislodgement is presumed, and a signal is sent to discontinue therapy and take other measures to insure the safety of the patient.

Another way to interlock the therapy machine and to insure the safety of the patient is to use a magnet on the tubing and a hall-effect sensor on the patient. As depicted in FIG. 6B, tubing 67 is equipped with a small magnet 68 or magnetizable material that is detectable by a hall-effect sensor. A hall-effect sensor 65 is mounted on the patient for detection of the magnet, with interlocks and safety features as discussed above. In this embodiment, a magnet could likely instead be located on the needle, but placing the magnet on the tubing should make detection by the hall-effect sensor easier, rather than in the metallic environment of the needle.

In another embodiment, detection may be accomplished by two or three sensors, and the needle or tubing may have one or more marks, for example, three marks spaced apart different distances. The sensors may be placed so that the marks align with their respective sensors only when the needle and tubing approach the fistula or other access site from a particular, proper direction. In this manner, the placement of the needle or tubing or both is very much an indicator of compliance. This would force compliance in both the location and orientation of the sensor, with respect to the tubing or the needle, before therapy can commence.

An example is depicted in FIG. 7. In this example, compliance system 70 includes three sensors or detector 76, 77, 78. The sensors may be optical sensors, proximity sensors, or hall-effect sensors. The tubing or needle 71 includes three features for detection. As discussed above, the features may be marks, such as dark, easily detectable marks, for optical detection. The features could instead be magnets or pieces of metal, or a combination of marks, magnets, or metal objects. A seen in the figure, features 72 and 73 are widely spaced, perhaps about 5 mm, about ½ inch, while features 73 and 74 are spaced more closely, about 2-3 mm, about ¼ inch. Of course, the embodiments of FIGS. 5-7 could also be used as dislodgement detectors themselves, without the array of photosensors discussed above.

Figure 8:
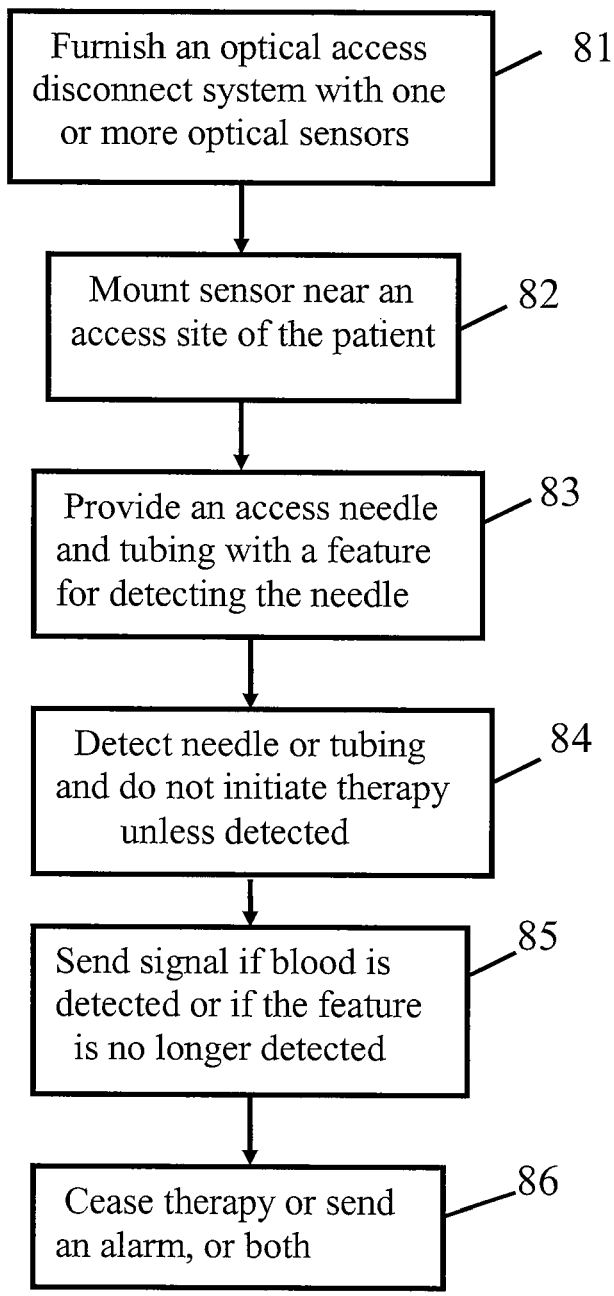
FIGS. 8 and 9 are flowcharts for methods of operating the sensors.
Figure 9:
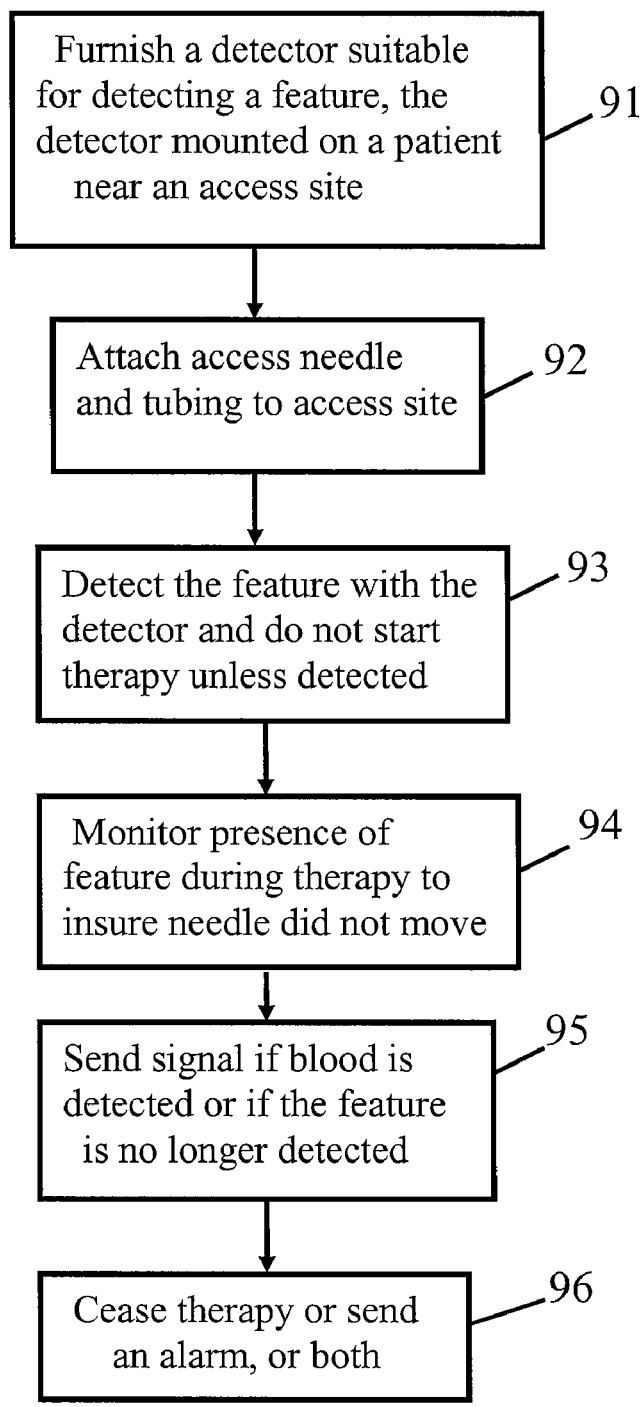

There are many ways to use the optical access disconnect sensors discussed above, and there are also many ways to use the needle or tubing presence sensors also. A few of these methods are depicted in FIGS. 8-9. In the method of FIG. 8, a first step 81 is to furnish an optical access disconnect system with one or more optical sensors. An optical sensor is a sensor that is able to detect light and output a signal in some relation to the light detected. The output signal need not be analog and it need not be proportional to the quanta of light detected. The optical sensor may include both an optical light emitter and an optical detector. An optical detector is also a sensor that is at least able to detect light and output a signal in some relation to the light detected. An optical sensor may be able to emit light as well.

In the second step 82 of the method of FIG. 8, one or more sensors are mounted near or adjacent an access site of the patient. The optical sensors should be very near the access site so that they can quickly detect blood leakage, and as will be discussed below, cause some action to be taken. The access needle and tubing for the access needle is then furnished 83. The needle or the tubing desirably includes a feature so that the needle or the tubing themselves may be detected. This aspect of embodiments of the invention can provide additional assurance to the patient of the safety of dialysis or other therapy to be provided. If this aspect is included, the computer software that controls the dialysis machine, such as a hemodialysis machine, may be programmed so that the therapy cannot begin until the needle or tubing is detected. That is, the therapy machine or device is interlocked so that the therapy or procedure cannot begin until the presence of the needle, or the tubing attached to the needle, is detected 84.

This requirement helps to insure that the patient and the needle are properly positioned, and that the therapy or procedure at least is begun correctly. As therapy begins, time passes and the needle may become dislodged as the patient moves, or as other circumstances arise that may disturb the peace and quiet of the procedure. In one embodiment, blood may be detected by one or more of the optical sensors. In the same or a different embodiment, the feature on the access needle or the tubing may cease to be detected, for example if the needle is dislodged from the access site. If either of these occur, a signal is sent 85 to a control module or to a communications module. The therapy machine, the communications module, or the control module may then take action 86 to cease therapy, to sound an alarm, to alert a care giver or to otherwise safeguard the health and safety of the patient.

Another method of sensing an access disconnect and protecting the patient is depicted in FIG. 9. In this method, a detector is furnished 91, the detector suitable for detecting a feature on an access needle or on tubing for connection to the needle. The feature, as discussed above, is detectable via an optical sensor, a proximity sensor, or a hall-effect sensor. The feature may be a mark, a metal object, or a magnet. The access needle and its tubing is then attached 92 to the access site. The detector then detects 93 the feature, and the therapy machine, such as a hemodialyis machine, is programmed or otherwise interlocked, such as by AND or OR circuits of the like, so that therapy cannot begin until the feature is detected.

Once the presence has been detected, therapy is begun and the detector monitors 94 the presence of the feature, to be sure that the needle, or the tubing attached to the needle, is not dislodged. In order to accomplish this, the detector can periodically run query to see if the feature is still present. The query may be run at intervals of about 0.5 seconds to about every 2 seconds, or other selected intervals, equivalent to a rate from about 0.5 Hz to about 2 Hz. Other rates may be used. If the feature is no longer detected on one of the queries, a signal may be sent 95. If a blood detection circuit is also being used, the signal may also be sent if blood is detected. The signal sent by the control circuitry then causes 96 therapy to cease, an alarm to be sent, or some other action to be taken.

Figure 10:
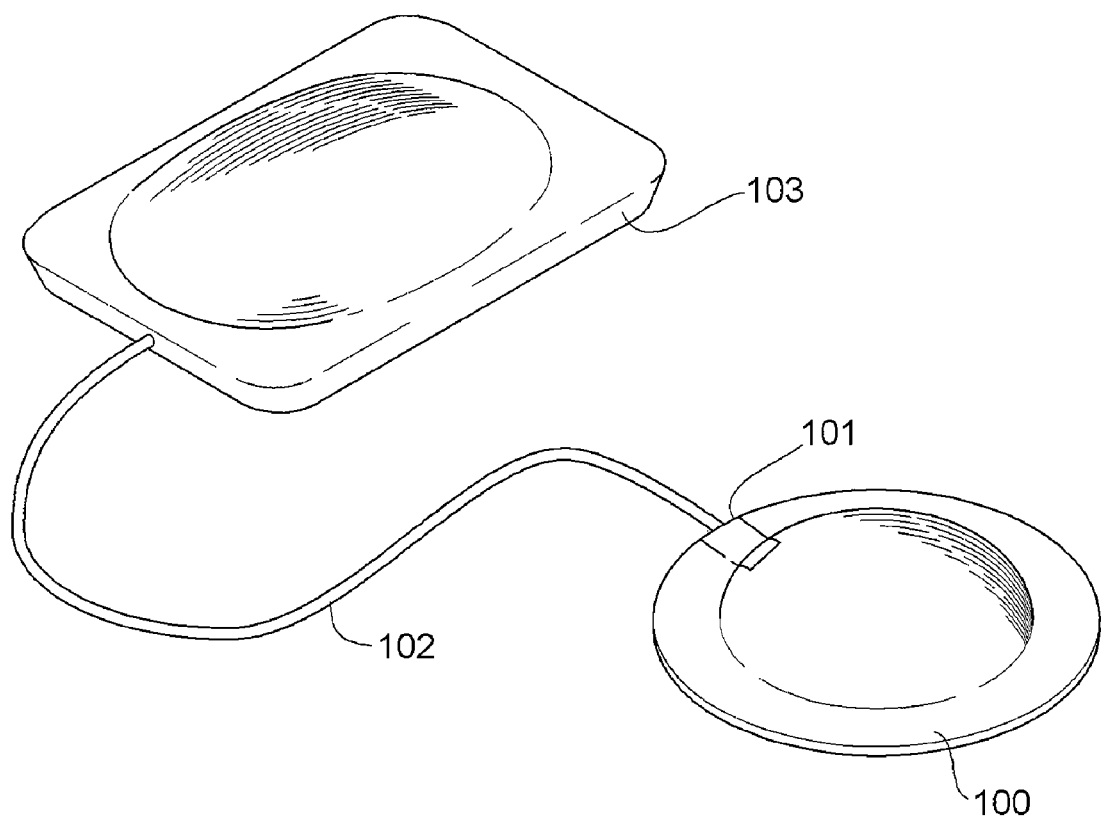
FIGS. 10-11 depict additional embodiments of an optical disconnect detection system.

There are still other embodiments that may use the optical sensors disclosed herein. Many of these additional embodiments are concerned with packaging and mounting the sensors to their best advantage on the patient. FIG. 10, for example, shows an embodiment of an access disconnect detection system in which there is a flexible mount 100 with a housing for mounting on the patient with a single optical sensor 101. The optical sensor is mounted on the patient as described above, with connecting cable or wiring 13 to a control unit 103 in a separate housing. Control unit 103 includes at least a power source and sufficient signal processing capability to pass on the signals or process data from the sensor to a remote processor (not shown).

Figure 11:
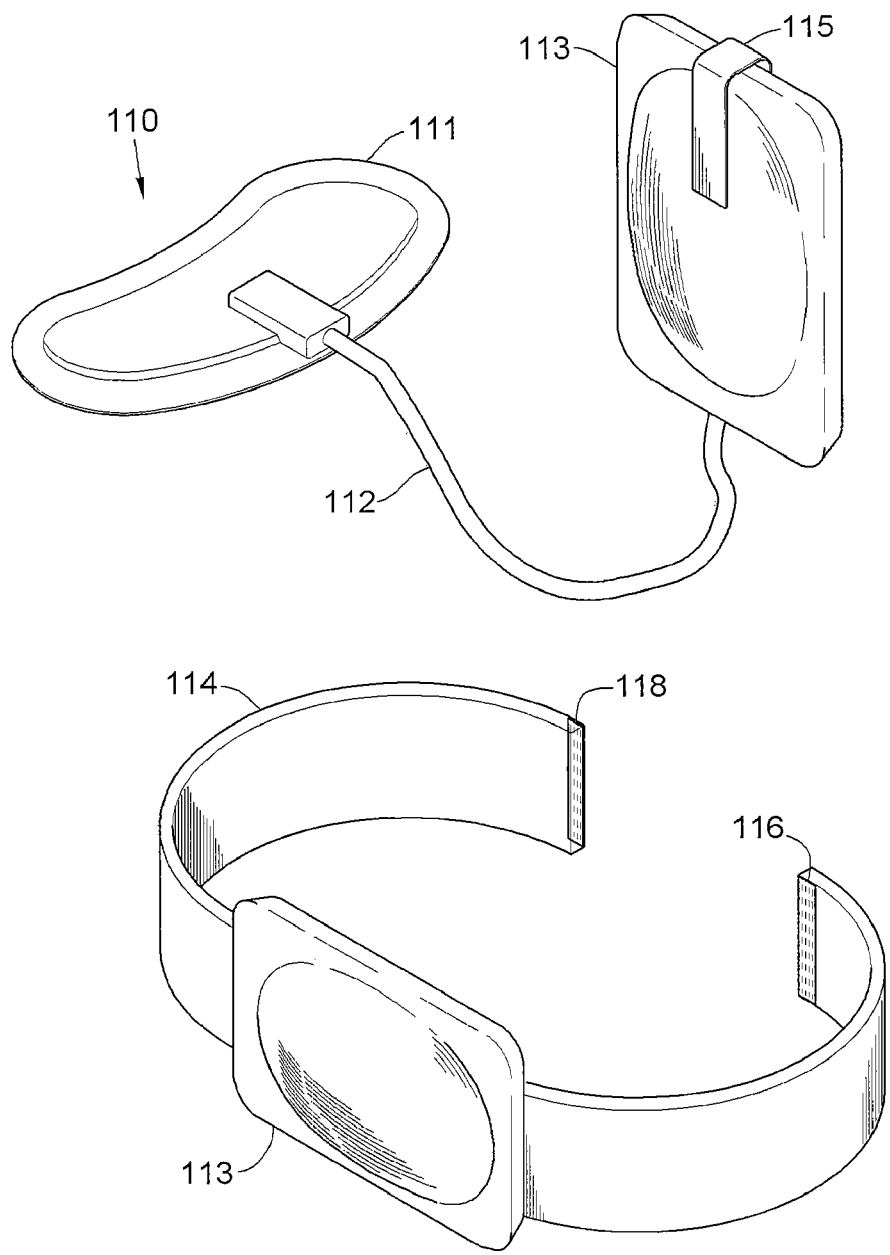

As shown in FIG. 11, the sensor mount 111 may take on other forms, such as the "butterfly" shape depicted. The form of mount 111 is intended for placement close to, but not atop, the access site, while mount 100 is intended for placement atop the access site. FIG. 11 also depicts two embodiments of the control unit. Control unit 113 may be equipped with a clip 115, as for attachment to a patient's gown or sleeve. Alternately, control unit 113 may be equipped with a wrist-band 114 for placement around a patient's wrist. End strips of hook-and-loop fasteners, such as those known under the trademark Velcro®, may be used.

Figure 12A:
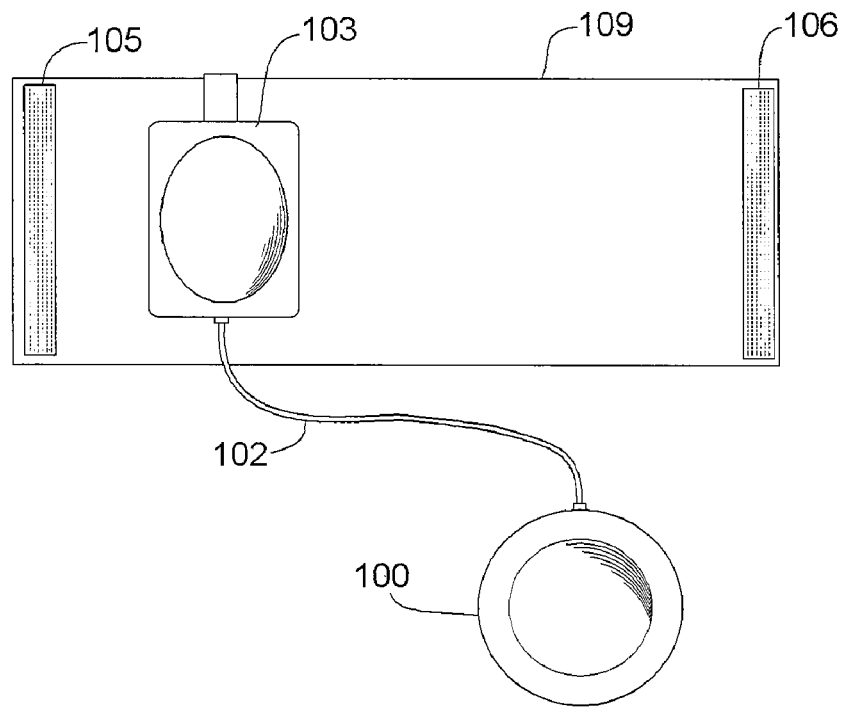
FIGS. 12A and 12B depict different ways to mount the sensors to the patient.
Figure 12B:
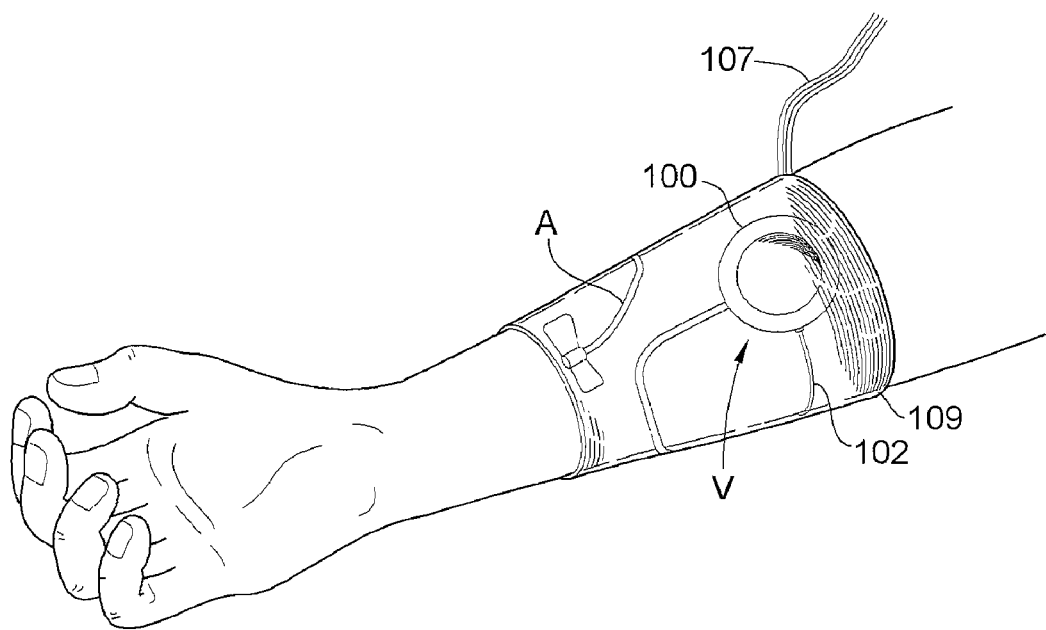

Another way to comfortably and conveniently place the sensors is depicted in FIGS. 12A and 12B. The top part of control unit 103 attaches to the outside of mounting band 109, control unit 103 still connected to sensor mount 100 via cable 102. Cable 102 is long enough, at least about 15 cm (about 1 foot) to conveniently attach the control unit to the patient's gown or sleeve. Mounting band 109, made of cloth or other suitable material, has strips of hook-and-loop fasteners on opposite sides and on the ends for attaching around the patient's arm P and around the access site, as depicted in FIG. 12B, which includes arterial access site A and venous access site V. Tubing 107 leads to and from the therapy machine.

Alternatively, the control unit may be miniaturized and integrated with the sensor in mount 100. There would be no need for a second portion or a tether/cable 102 and control unit 103, because the control unit, with necessary circuitry, battery, and wireless transmitter, would be integrated into a single sensor mount housing. The integrated unit would then be placed adjacent or over the access site, and would transmit wirelessly back to a remote controller or therapy machine.

Figure 13:
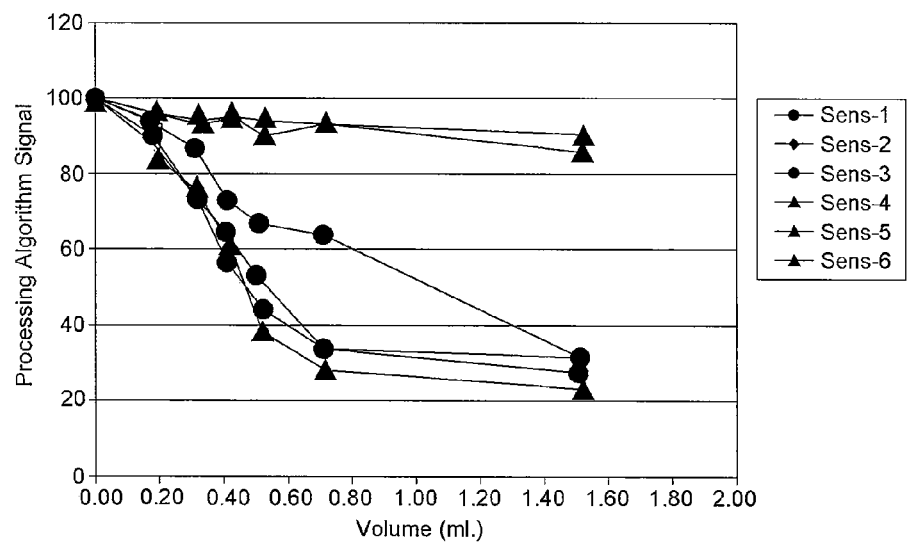
FIGS. 13-15 are graphs depicting optical sensor leak test performance.
Figure 14:
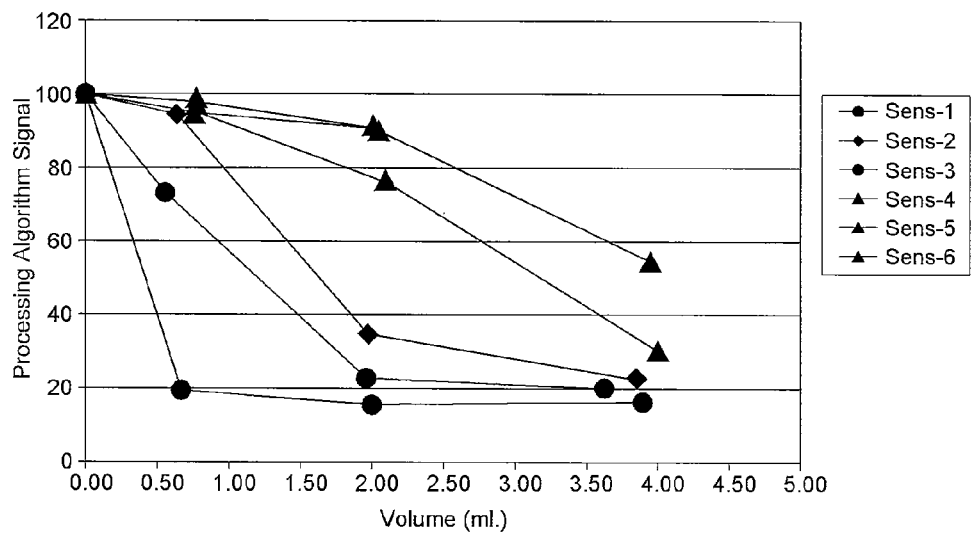
Figure 15:
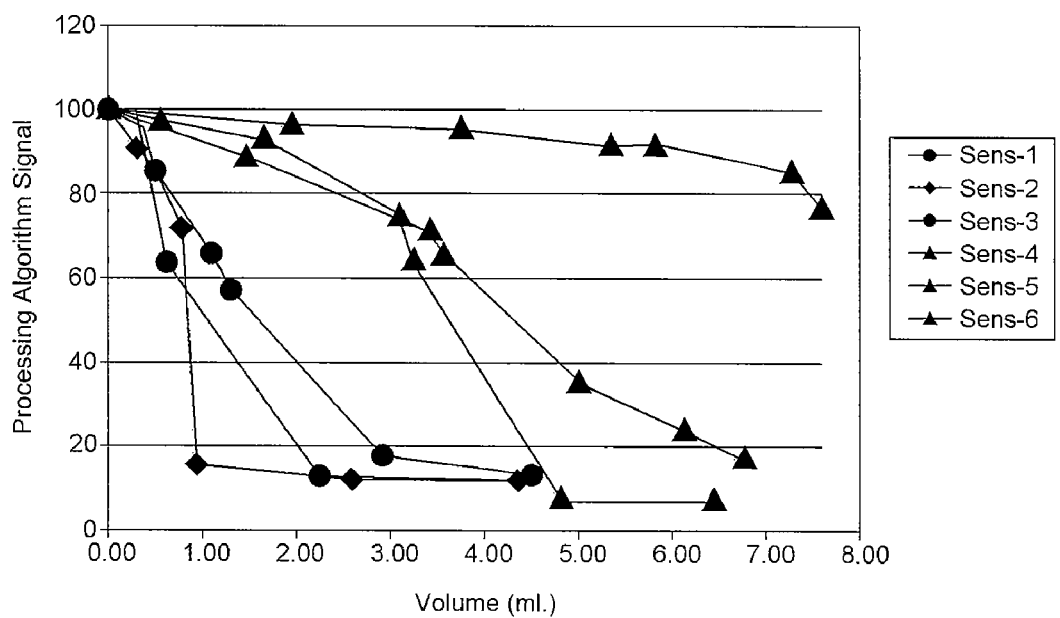

Testing has been conducted on the use of the optical sensors to detect blood, and the results of the testing are depicted in FIGS. 13-15. The tests were conducted using bovine blood, with characteristics, 40-45 hematocrit (Hct), similar to those of human blood. The mount of FIG. 3 was used, with six Hamamatsu S5821-2 photodiodes. These photodiodes have a peak sensitivity at about 960 nm, which is near a wavelength reflected from blood. Room lighting was used as the light source.

The mount was placed over an access needle, with needle clamps holding the needle, and a syringe pump with a luer connection to the needle. Gauze and tape were placed atop this structure, and the sensors were mounted on top of the tape. Three blood leak flow rates were used, 0.1 ml/min (FIG. 13), 1 ml/min (FIG. 14), and 10 ml/min (FIG. 15). Reflectance signals from the six sensors were monitored as the blood wicked into the gauze pad. Sensor output values in these graphs have been normalized to the first data point recorded (no blood present) for each sensor.

Sensors 1-3, marked with circles or diamonds on each of the graphs, were the inner ring of the mount, closer to the leak, while sensors 4-6, triangles on the graphs, were on the outer ring, further from the leak. As can be seen in FIG. 13, blood with a very slow leak, 0.1 ml/min, was first detected at about 0.20 ml, or about 2 minutes into the test. In FIG. 14, with a leak rate 10 times that of FIG. 13, blood was first detected at about 0.5 ml. or about ½ minute into the test. In FIG. 15, with a much higher leak rate, 100 times that of FIG. 13 and 10 times that of FIG. 14, blood was first detected at about 0.5 ml, or about 3 seconds into the test. In all three tests, blood was first detected when the accumulated volume was 0.5 ml or less.

The results of the testing also demonstrate that one sensor alone can detect the leak shortly after the gauze begins to absorb blood, especially if it is placed close to the access site. However, other systems may utilize two or more sensors. This redundancy will add to the reliability of the access disconnect system, if any one particular sensor is deactivated or otherwise fails to perform, e.g., if a wire is accidentally shorted or clipped. It is also clear from these test results that the closer the sensor or sensors are placed to the access site, near the potential for leakage, the more quickly blood is sensed. This is perhaps most dramatically shown in FIG. 15. In FIG. 15, with a high blood leakage rate of 10 ml/min, all three inner sensors (circles or diamonds on graph) detected blood very quickly, within about 3-4 seconds. The outer sensors, shown by the triangles on the graph, took about twice as long or longer, and they also took much more time for the reflectance values to drop precipitously. This may be due to a greater volume of leakage fluid required to detect absorbance/reflectance changes as distance increases from the access site.

Without being bound to any particular theory, it is believed that as blood was absorbed into the gauze, more light was absorbed by the blood than was reflected by the gauze. Thus, the photodiodes did not detect as much light and as the reflectance fell off, so did the output voltage of the sensor. These particular photodiodes are more sensitive to the higher wavelengths. In other embodiments, such as those using the TAOS photodiodes described above, the sensor may be more attuned to another wavelength, such as red (630 nm, model TRS1722), green (567 nm, TRS1755) or blue (470 nm, TRS1766). Light of other wavelengths may be used.

It should be understood that various changes and modifications to the presently preferred embodiments described herein will be apparent to those skilled in the art. For example, embodiments have been described as mounting the sensor on the patient, with a cable connecting a separate electronics module. It is clear that this design favors comfort of the patient, limiting the amount of hardware, and thus discomfort, on the patient.

Any of the devices that are described as remote could instead be mounted on the patient, but the patient would suffer some loss of comfort and independence. In another example, it is clear that the greatest use for embodiments is in a venous access needle; nevertheless, a arterial access needle may also be equipped with a disconnect detection system as described herein. Such changes and modifications can be made without departing from the spirit and scope of the present subject matter and without diminishing its intended advantages. It is therefore intended that such changes and modifications be covered by the appended claims.

What is claimed is:

1. An optical access disconnect system, comprising:
at least one first optical detector;
a needle detector for detecting a venous needle;
a mount suitable for mounting the at least one first optical detector and the needle detector;
signal processing circuitry, the circuitry operably connected to the at least one first optical detector and the needle detector; and
a communications circuit connected to the signal processing circuitry, wherein the mount, the at least one first optical detector, and the needle detector are configured for positioning adjacent a dialysis access site for detecting a presence of blood of a patient and for detecting a presence of a venous needle, respectively, wherein the needle detector is a second optical detector positioned and arranged to look for movement of a mark or an object on the venous needle or on tubing connected to the venous needle.

2. The system of claim 1, wherein the communications circuit comprises a wired or wireless connection to a controller.

3. The system of claim 1, further comprising at least one light source connected to the signal processing circuitry and configured to emit light for detection by the at least one first optical detector.

4. The system of claim 1, wherein the at least one first optical detector comprises at least two optical detectors, and further comprising at least one light source configured to emit light for detection by the at least two optical detectors.

5. The system of claim 1, wherein the at least one first optical detector comprises at least two optical detectors, and further comprising at least two light sources of different wavelengths connected to the signal processing circuitry and configured to emit light for detection by the at least two optical detectors, wherein one of the light sources optionally emits light with a wavelength of about 425 nm.

6. The system of claim 1, wherein the signal processing circuitry further comprises an analog-to-digital converter for converting analog signals from the at least first optical detector into digital signals for further data processing by a local or remote controller.

7. The system of claim 1, further comprising an output device operably connected to the signal processing circuitry or a controller for the signal module for sending a signal if the at least one first optical detector detects blood leakage.

8. The system of claim 1, wherein the signal processing circuitry comprises at least one of signal analog-to-digital conversion processing, signal data conversion, and additional data processing.

9. The system of claim 1, further comprising an interlock for preventing initiation of dialysis therapy if the needle detector does not detect the presence of the venous needle.

10. An optical access disconnect system, comprising:
at least one optical sensor;
a needle sensor for detecting an access needle;
a mount suitable for mounting the at least one optical sensor and the needle sensor on a patient, wherein the mount, the at least one optical sensor, and the needle sensor are configured for positioning adjacent an access site for detecting respectively a presence of blood and a presence of the access needle, wherein the needle sensor is a second optical sensor positioned and arranged to look for movement of a mark or an object on the access needle or on tubing connected to the access needle;
signal processing circuitry operably connected to the at least one optical sensor and the needle sensor;
a communications circuit connected to the signal processing circuitry; and
an output device connected to the communications circuit or to the signal processing circuitry, the output device configured for sending a signal if blood is detected.

11. The optical access disconnect system of claim 10, wherein the access site is a dialysis access site.

12. The optical access disconnect system of claim 10, wherein the mount comprises a flexible pad.

13. The optical access disconnect system of claim 12, wherein the pad further comprises an absorbent material adjacent the at least one optical sensor.

14. The optical access disconnect system of claim 10, wherein the signal processing circuitry is mounted in a housing separate from the at least one optical sensor.

15. The optical access disconnect system of claim 10, further comprising an interlock for preventing initiation of therapy if the needle sensor does not detect the presence of the access needle.

16. An optical access disconnect system, comprising:
at least one optical sensor;
a mount suitable for mounting the at least one optical sensor, wherein the mount and the at least one optical sensor are configured for positioning adjacent a dialysis access site on a patient for detecting a presence of blood;
signal processing circuitry operably connected to the at least one optical sensor;
a detector for detecting a presence of a needle adjacent the access site, the detector operably connected to the signal processing circuitry or a control circuit in communication with the signal processing circuitry, wherein the detector is an optical detector positioned and arranged to look for movement of a mark or an object on the needle or on tubing connected to the needle; and
a communications circuit connected to the signal processing circuitry.

17. The optical access disconnect system according to claim 16, further comprising an output device for raising an alarm or ceasing dialysis if blood is detected or if the needle is dislodged.

18. The optical access disconnect system according to claim 16, wherein the mount is further configured to mount the detector.

19. The optical access disconnect system according to claim 16, further comprising an optical filter.

20. The optical access disconnect system according to claim 16, further comprising an interlock for preventing initiation of dialysis therapy if the detector does not detect the presence of the needle.

* * * * *